United States Patent [19]

Bonadio

[11] 4,182,754

[45] Jan. 8, 1980

[54] ORAL INGESTION OF INDIUM

[76] Inventor: George A. H. Bonadio, 373 East Ave., Watertown, N.Y. 13601

[21] Appl. No.: 869,579

[22] Filed: Jan. 16, 1978

Related U.S. Application Data

[63] Continuation-in-part of Ser. No. 732,491, Oct. 14, 1976, abandoned.

[51] Int. Cl.$^2$ ..................... A61K 33/24; A61K 31/28
[52] U.S. Cl. ..................................... 424/131; 424/287
[58] Field of Search ................................ 424/287, 131

[56] References Cited

PUBLICATIONS

Chemical Abstracts 52:13116(d) (1958).
"Town & Country News Gouverneur," Jun. 30, 1976.

Primary Examiner—Jerome D. Goldberg
Attorney, Agent, or Firm—Ostrolenk, Faber, Gerb & Soffen

[57] ABSTRACT

Indium and its compounds are used to normalize the activity of the thyroid gland.

4 Claims, No Drawings

ORAL INGESTION OF INDIUM

This application is a continuation-in-part of my prior application Ser. No. 732,491, filed Oct. 14, 1976 and now abandoned.

BACKGROUND OF THE INVENTION

Only eleven elements make up more than 99% of the human body. Hydrogen, carbon, nitrogen, oxygen, phosphorus and sulfur are the building block for proteins, fats, carbohydrates and nucleic acids. Calcium, potassium and magnesium are essential parts of all cells. Sodium and chlorine are present as salts in body fluids. The rest of the human body, less than 1%, consists of trace elements in amounts from several hundred parts per million to less than a few parts per billion.

Nutritional research has established that certain of the trace elements are essential to the existence of man. Up until 1957, only seven trace elements were recognized as essential: iron, iodine, copper, manganese, zinc, cobalt and molybdenum. Since that time seven additional elements have been added, namely, selenium, chromium, tin, vanadium, fluorine, silicon and nickel. It is possible that arsenic may also be an essential trace element.

These "trace" elements are believed to function in four ways. They help move common elements throughout the body, they maintain enzymatic activity, they assist the action of hormones and it is believed that they influence nucleic acid metabolism.

Indium is a soft white metal with a bluish tinge which is primarily found in the ores of zinc and lead and also found in oil shale. Indium and its compounds have heretofore been employed chiefly in industrial uses such as bearing alloys, dental alloys and semiconductor electronics. Indium is not an essential element since it is not required by the human body for proper functioning. In general, before a "trace" element can be considered essential, it must be present in either the biosphere, the newborn and/or excreted in milk, organs and tissues or in the ova. Indium is not found in any of these alternatives and therefore has been routinely bypassed for any meaningful investigation concerning the beneficial results from use in "trace" amounts in man.

The effect of certain indium compounds administered by subcutaneous or intravenous administration to lower animals has received some cursory investigation.

I have now found that indium and its absorbable compounds have a beneficial effect similar to that of the essential trace elements even though indium is not an essential element. The beneficial effect can be realized when the indium and its compounds are administered orally in "trace" amounts. In particular, indium has been found beneficial in the normalization and/or enhancement of the glandular feedback control of the thyroid gland.

It is accordingly the object of this invention to provide a new nutritional supplement which is particularly useful in the normalization and/or enhancement of the activity of the thyroid gland. This and other objects of the invention will become apparent to those skilled in the art from the following detailed description.

SUMMARY OF THE INVENTION

This invention relates to a new nutritional supplement and its use and more particularly relates to the use of indium and its absorbable compounds in trace amounts administered orally for the normalization and/or enhancement of the activity of the thyroid gland.

DESCRIPTION OF THE INVENTION

Indium is a member of the heavy metals and is a soft white metal with a bluish tinge. Although scarce, indium and many of its compounds are commercially available. While the indium in powdered, pellet or granular form can be used, its reactions with the primary metallic acids in the stomach are apt to be of irregular predictability thereby producing variable and unpredictable absorption in the body system. Additionally, indium's reaction with those metallic acids in the stomach can produce discomfort to the user. It is therefore preferred to employ the indium in the form of one of its digestable compounds. Such compounds include indium acetate, carbonate, chloride, gluconate, phosphate, palmitate, sulphate, and various chelates. Indium acetate is the preferred salt because it is commercially available at moderate prices, readily absorbable, high in purity and stability, easy to handle, of low bulk, low odor and low taste, and readily formed into mixtures with other nutritional supplements. In accordance with this invention, the indium or its compounds are administered by the oral route. This route has the advantages that it does not require medical supervision or facilities, can be performed by the individual user, does not involve extensive procedures and results in less psychological anguish. The indium can be administered in pill, tablet, capsule or solution form and can, if desired, be incorporated into a mixture of other nutritional supplements such as a vitamin and/or mineral preparation.

Indium, as a supplement, is quite similar to the essential trace elements in that it has a rather narrow "concentration window". Above the window, undesirable side effects are realized and if the amount is too far in access of the window, indium, as with the essential trace elements, is toxic. Below the concentration window, administration is ineffective, but, in distinction to the essential elements, is not life threatening. The concentration window in the case of indium or its compounds has a typical range of about 100 to one. The administered amount can be from about 0.0037 to about 0.37 mg/kg of body weight and is preferably about 0.12 mg/kg. In absolute numbers, the administered amount is about 0.25–25.0 mg, daily, which may be divided into meals or grouped up to three days.

The indium interacts with the body's metabolism by normalizing and/or enhancing the glandular feedback controls of the thyroid gland. In those individuals who do not need such normalizational and/or enhancement, the oral administration does not adversely affect thyroid activity. A small amount of indium acetate was orally administered to an individual who had a thyroid condition requiring him to take regular thyroid hormone supplements. After a period of regular dosages of indium acetate, the distinctive symptoms of thyroid hormone overdosage began to appear. The normal amount of thyroid hormone supplement was then reduced while the indium acetate administration was continued. A short time later, with more indium, the symptoms of thyroid hormone overdosage again began to appear and the thyroid hormone supplement was reduced again. After about six months of daily oral ingestion of the indium acetate, an optimum level of indium was discovered and the thyroid hormone supplement was eliminated completely without any adverse effects. The individual also reported that it took much greater quantities of alcohol to obtain a "high" feeling and that his previously normally low blood temperature had increased to a point closer to the accepted "normal" level.

I have discovered from various volunteer users of indium acetate that effects have included normalization of the thyroid gland, normalization of body temperature, increased detoxification rate of the liver, enhanced mental functions, hardening of fingernails, increased orgasmic fluids, enhanced body immunity systems, and an overall enhanced "feeling of well being". Some of these reported results may be attributed to a placebo type effect upon the various users.

Various changes and modifications can be made in the process and products of this invention without departing from the spirit and scope thereof. The various embodiments which have been described above were set forth in order to further illustrate the invention but were not intended to limit it.

I claim:
1. A method of reducing or eliminating the need for thyroid hormone supplement in a human receiving such supplement by administering orally indium or a digestible compound thereof selected from the group consisting of indium acetate, indium carbonate, indium chelate, indium chloride, indium gluconate, indium phosphate, indium palmitate and indium sulphate in a daily average amount of about 0.25–25.0 mg.

2. The method of claim 1 wherein said indium compound is indium acetate.

3. The method of claim 2 wherein said amount is about 8.0 mg as indium.

4. The method of claim 1 wherein said indium or its compounds is administered in admixture with nutritional supplements.

* * * * *